United States Patent [19]

Kessel

[11] 4,103,423

[45] Aug. 1, 1978

[54] ORTHODONTIC BRACKET

[76] Inventor: Stanley P. Kessel, Suite 411, 3325 Hollywood Blvd., Hollywood, Fla. 33021

[21] Appl. No.: 774,447

[22] Filed: Mar. 4, 1977

[51] Int. Cl.² .............................................. A61C 7/00
[52] U.S. Cl. .................................................... 32/14 A
[58] Field of Search ................... 32/14 A; 24/249 LL, 24/248 B, 132 WL

[56] References Cited

U.S. PATENT DOCUMENTS

| 1,504,964 | 8/1924 | Newland | 24/248 B |
| 3,123,913 | 3/1964 | Rubin | 32/16 A |

Primary Examiner—Robert Peshock
Attorney, Agent, or Firm—Birch, Stewart, Kolasch & Birch

[57] ABSTRACT

An orthodontic edgewise arch bracket locking mechanism is described. The bracket locking mechanism includes a conventional edgewise arch bracket body with four occlusal tie wings, a handle and a locking hook. In addition, the arch bracket includes a slot designed to hold a conventional arch wire. The handle, locking hook and two of the tie wings are pivotally positioned in an over-center arrangement so that when the free end of the locking hook is positioned adjacent to the other tie wings and the handle is moved to a position parallel to the bracket body, the free end of the locking hook engages the other tie wings in a cam-like action that snaps it securely against the bracket body holding an arch wire firmly within the bracket slot. The bracket locking mechanism may be opened by moving the handle to a position perpendicular to the bracket body thereby releasing the locking hook.

11 Claims, 5 Drawing Figures

ORTHODONTIC BRACKET

BACKGROUND OF THE INVENTION

1. Field of the invention

The present application relates to a device utilized in the specialty of orthodontics and more particularly to an orthodontic bracket used in fastening orthodontic arch wires to a tooth so that the tooth may be properly positioned within the dental arch. In addition, the present application relates to an orthodontic edgewise arch bracket locking mechanism which includes a handle and a locking hook which are pivotally secured to each other and to two of the tie wings of a conventional edgewise arch bracket. The handle, locking hook and the two tie wings are privotally positioned in an overcenter arrangement so that when the locking hook is positioned adjacent to the other tie wings and the handle is moved to a position parallel to the body of the arch bracket, the locking hook is snapped in a cam-like action against the bracket body holding an arch wire firmly within a slot in the bracket body.

2. Description of the Prior Art

Heretofore, the most popular and universally employed orthodontic appliance has been the edgewise arch. For nearly fifty years, an arch wire has been secured to a bracket portion of the edgewise arch to properly position certain teeth within the dental arch. The arch wires of the prior art were secured to the bracket portion by means of thin ligature wires or tiny elastic members secured to the four tie wings of an arch bracket. Securing these prior art ligature wires required the following steps:
  a. sliding the ligature wire under the four tie wings of an arch bracket;
  b. twisting the ligature tightly over the arch wire;
  c. cutting the excess ligature leaving a small twisted pig-tail, and
  d. tucking the pig-tail under the arch wire to prevent laceration of a patient's lips, check or tongue.

To remove these prior art ligature wires necessitated carefully cutting the ligatures with very sharp nippers and removing the remnants. This procedure was sometimes dangerous to the aforementioned tissues.

The use of prior art tiny elastic members required the careful spreading of the members so as to fit over the four tie wings of an arch bracket. The disadvantages of these members included an inability to retain an arch wire firmly within the entire slot of an arch bracket, unless the wire itself conformed to the slot in a passive state. It is known that the flexibility of the arch wire is the most efficient means of transmitting a corrective force through the bracket and thus to the tooth itself. It is of paramount importance that the arch wire be secured to the arch bracket and fully seated in the bracket slot when the arch wire is in an active state. Prior to the present invention, the proper securement of the arch wire was only accomplished by use of ligature wires. Elastic members were never fully satisfactory to secure the arch wire.

In addition, since both wire ligatures and elastic members frictionally grip the arch wire, they do not readily permit sliding of the arch brackets and teeth along the arch wire, which is an important exigency in certain phases of orthodontic procedures.

Other prior art devices were designed to overcome the disadvantages of the use of wire ligatures and elastic members. One prior art device, U.S. Pat. No. 3,748,740 issued to A. J. Wildman, was designed to retain one or more arch wires in a groove by means of a self-latching, C-shaped hook. This prior art device was a complete departure from the conventional edgewise bracket including tie wings used by most orthodontists. Since the Wildman device was such a drastic departure from the traditional edgewise bracket, it is not believed that a conservative and doctrinaire edgewise orthodontist would utilize this device.

Another prior art device, U.S. Pat. No. 3,574,942 issued to J. B. McCabe, was designed to retain an arch wire within a recess by means of a lateral projection which may be rotated into the retaining position. Again, this device was a complete departure from the conventional edgewise bracket including tie wings.

Still another prior art device, U.S. Pat. No. 3,205,577 issued to J. A. Linde, was designed to releasably lock the rear support of an orthodontic appliance against lateral movement while permitting the appliance to have free longitudinal movement. While this device apparently shows a locking mechanism, it was not intended to be used with a conventional edgewise bracket as in the present invention.

SUMMARY OF THE INVENTION

It is an object of the present invention to provide an improved edgewise bracket that greatly simplifies securement of arch wires thereto.

It is an object of the present invention to eliminate most of the routine ligature tying or elastic placement by providing a locking mechanism that locks the arch wire into the bracket slot in one step.

It is an object of the present invention to drastically shorten the time needed to properly administer treatment to an orthodontic patient.

Another object of the present invention is to eliminate dangerous wire ligature cutting and removing.

A further object of the present invention is to increase the comfort of the patient by eliminating the wire ligature pig-tails which can easily lacerate adjacent mouth tissues.

A still further object of the present invention is to provide for the arch bracket to slide easily along the arch wire where necessary but to retain the capability to be able to conventionally tightly secure the arch wire within the slot by use of ligature wire should the need arise.

Another object of the invention is to provide for the use of traditional rotating springs and other edgewise arch adjuncts which are conventional in this art.

These and other objects of the present invention are fulfilled by constructing an edgewise arch bracket locking mechanism which includes a handle and a locking hook pivotally secured to each other and to two of the occlusal tie wings of a conventional edgewise arch bracket. The edgewise arch bracket includes four tie wings and a slot in the bracket body. The handle, locking hook and the two tie wings are pivotally positioned in an overcenter arrangement so that when the free end of the locking hook is positioned adjacent the other tie wings and the handle is moved to a position parallel to the bracket body, the locking handle snaps in a cam-like action against the bracket body holding the arch wire within the slot in the bracket.

Other objects and further scope of applicability of the present invention will become apparent from the detailed description given hereinafter. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENT

Figure 1:
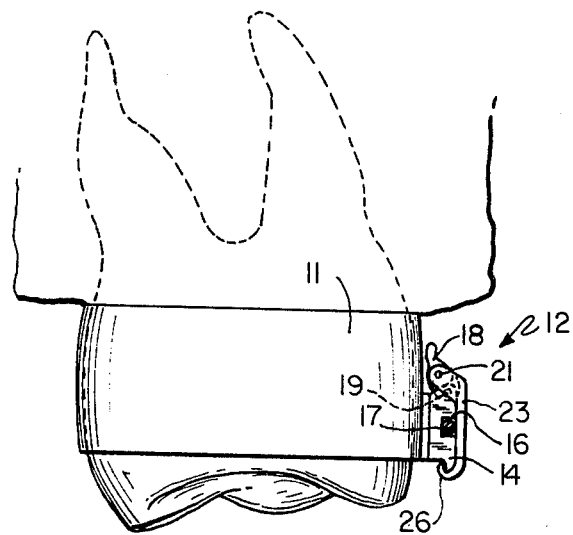
FIG. 1 is a side view of the edgewise arch bracket locking mechanism constructed in accordance with the principles of the present invention as shown in the fully locked position.

Referring in detail to FIG. 1, there is illustrated an orthodontic edgewise arch bracket locking mechanism generally indicated by 12, which includes an orthodontic backing or band 11 and tie wings 14. The orthodontic backing or band 11 is designed to be attached to the tooth of a patient.

The bracket locking mechanism includes a handle 18 and a locking hook 23 pivotally secured to each other by the connecting pin 21 and pivotally attached to the occlusal tie wings by means of the attaching pin 19. The free end 26 of the locking hook 23 is designed to mate with the free end of the occlusal tie wings 14. It is to be understood that throughout this application the term occlusal tie wings may be readily interchanged with the term gingival tie wings depending upon the relative positioning of the edgewise arch bracket on the patients' tooth. As shown in FIG. 1, the bracket locking mechanism is in the closed position thereby locking the arch wire 17 within the bracket slot 16. It should be noted that the over-center arrangement between the connecting pin 21 and the attaching pin 19 achieves a locking relationship between the locking hook 23 and the occlusal tie wings 14 when the handle 18 is moved to the locking position.

Figure 2:
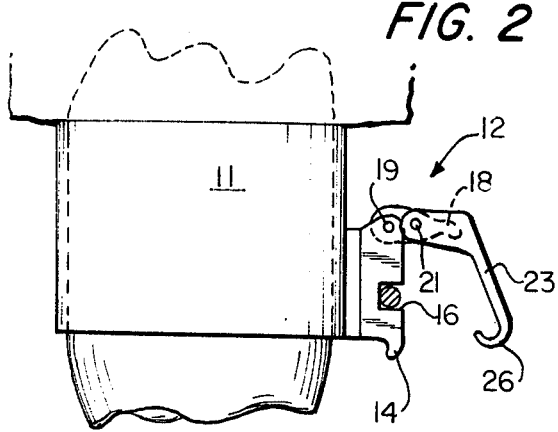
FIG. 2 is a side view of the edgewise arch bracket locking mechanism constructed in accordance with the principles of the present invention as shown in the fully opened position.

Referring in detail to FIG. 2, there is shown a bracket locking mechanism generally indicated by 12 which is in the fully opened position. The handle 18 is shown pivotally connected to the occlusal tie wings 14 by means of the attaching pin 19. The locking hook 23 is shown pivotally connected to the handle 18 by means of the connecting pin 21. The slot 16 is designed to receive an arch wire 17.

Figure 3:
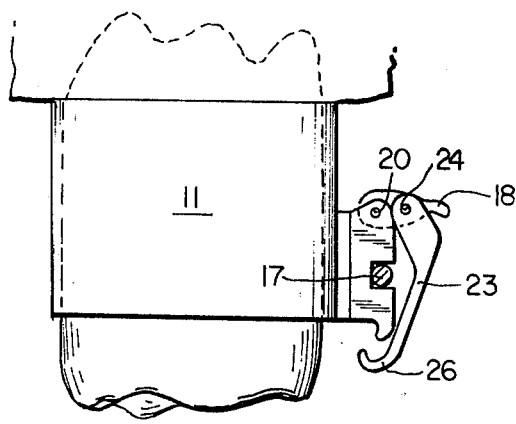
FIG. 3 is a side view of the edgewise arch bracket locking mechanism as shown in the position prior to movement to the locked position.

Referring in detail to FIG. 3, an orthodontic edgewise arch bracket locking mechanism is shown in the position prior to movement of the handle to the locked position. The arch wire 17 is positioned in the slot and the free end 26 of the locking hook 23 is positioned to mate with the occlusal tie wings 14 when the handle 18 is moved to the locking position. It should be noted, that as the handle 18 is snapped upwardly the connecting pin 21 is moved to an over-center relationship relative to the attaching pin 19 to thereby lock the locking hook 23 to the occlusal tie wings.

Figure 4:
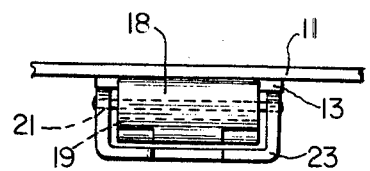
FIG. 4 is a top plan view of the present invention as shown in FIG. 1.

FIG. 4 illustrates a top view of the orthodontic edgewise arch bracket locking mechanism shown in the locked position. This figure shows that the connecting pin 21 is positioned in an over-centered relationship relative to the attaching pin 19.

Figure 5:
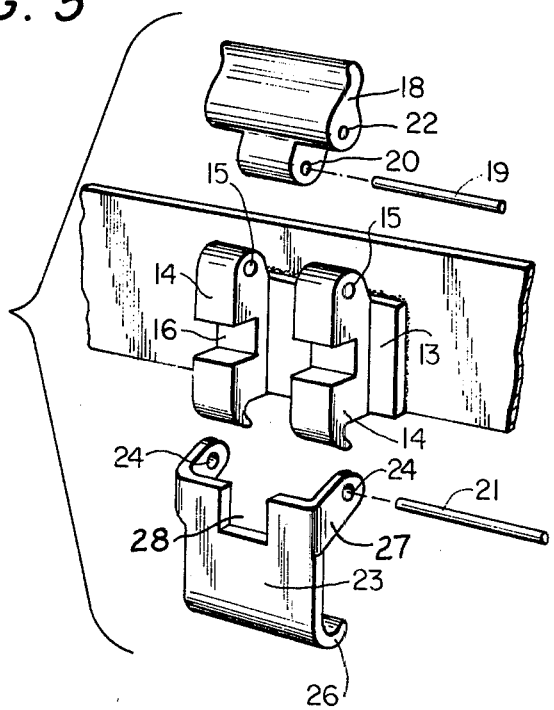
FIG. 5 is an exploded view of the individual components constructed in accordance with the principles of the present invention.

Referring now in detail to FIG. 5, there is illustrated an exploded view of the orthodontic edgewise arch bracket locking mechanism. The handle portion 18 is shown to include the connecting hole 22 and the attaching hole 20. The occlusal tie wings 14 include attaching holes 15, slots 16 and the free end portion of the occlusal tie wings shown on the opposite end from the attaching holes 15. The locking hook 23 is shown to include connecting holes 24 which are located on the locking hook arms 27. Also, the locking hook 23 includes an opening 28 into which the handle portion 18 may freely rotate. In addition, the locking hook 23 includes a free end 26 which is designed to mate with the free end portion of the occlusal tie wings.

To construct a preferred embodiment of the present invention, one would pivotally position a handle member to two occlusal tie wings of a conventional edgewise arch bracket. A locking hook member would be pivotally attached to the handle member in an over-center arrangement. The locking hook member would be designed to include a free end portion that would mate with the free end portion of the occlusal tie wings. The handle portion and the locking hook portion would be pivotally connected in an over-center arrangement so that when the free end of the locking hook member is positioned adjacent to the free end of the occlusal tie wings and the handle is moved to the locking position, the locking hook would be snapped into a locking engagement with the occlusal tie wings.

In operation, an orthodontist would position the backing or band 11 on the tooth of a patient. The handle and the locking hook are moved to the opened position to permit the positioning of an arch wire within the slot 16. Upon positioning of the arch wire within the slot, the handle is moved to the locking position thereby snapping the locking hook in a cam-like manner thereby locking the hook to the occlusal tie wings.

It should be noted, that the drawings illustrate one operative mode of the orthodontic edgewise arch bracket locking mechanism of the present invention wherein the handle member is positioned adjacent to the gum or gingival line of a patient. In addition, it should be understood that the orthodontic edgewise arch bracket locking mechanism of the present invention may just as readily be mounted to the tooth of the patient by positioning the free end of the locking hook adjacent the patients gum or gingival line and, correspondingly, the handle portion adjacent the biting surface of the patients tooth.

Finally, the orthodontic edgewise arch bracket locking mechanism of the present invention is a slight departure from the conventional edgewise arch bracket body. The present invention readily permits sliding of the arch brackets and teeth along the arch wire, which is an important exigency in certain phases of orthodontic procedures. The locking mechanism comprises a hook which snaps over the tie wings of a conventional edgewise bracket, covering the open end of the slot in the bracket body and thereby locking the arch wire within the slot but still permitting it to slide. If the orthodontist cannot immediately seat the arch wire within the slot or if he wishes to tie one or more teeth tightly to the arch so that they cannot slide, he would merely twist a ligature wire tightly around one or both brackets leaving the free ends to dangle outside the mouth of the patient. The locking mechanism would then be snapped shut effectively securing the ligature wire to the brackets. The free ends of the ligature wire may then be brought over and under the arch wire and twisted tightly thereto, thereby moving the tooth toward the arch wire. When the tooth is in sufficient proximity to the arch wire to enable the seating of the arch wire within the slot in the brackets, the ligature wire may be abandoned in favor of retaining the arch wire exclusively by means of the locking mechanism.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. An orthodontic appliance comprising:
   a bracket projecting from a tooth band and including two spaced ends;
   a handle privotally attached to one of said spaced ends of said bracket;
   a locking hook pivotally attached to said handle in an over-center relationship;
   whereby as the handle is rotated to a locking position, the locking hook engages the other spaced end of the bracket and is locked thereto.

2. An orthodontic appliance according to claim 1, wherein the bracket projecting from the tooth band includes means for retaining an arch wire.

3. An orthodontic appliance according to claim 2, wherein the means for retaining an arch wire comprises a slot positioned between the two spaced ends.

4. An orthodontic appliance according to claim 1, wherein the bracket comprises spaced occlusal or gingival tie wings to which the handle is pivotally attached and to which a free end of the locking hook is engageable and locked thereto.

5. An orthodontic appliance according to claim 3, wherein the slot positioned between the two spaced ends is covered by the locking hook in the locked position, thereby slidably retaining an arch wire within the slot.

6. An orthodontic appliance for supporting an arch wire from a tooth band comprising:
   a bracket projecting outwardly from the tooth band including first and second spaced portions;
   a handle pivotally attached to said first portion of the bracket;
   a locking hook pivotally attached to said handle in an over-center relationship;
   said locking hook including means for mating with the second portion of said bracket;
   whereby as the handle is rotated to a locking position and the locking hook is moved through the over-center pivotal relationship, the means for mating the second portion of said bracket engages said second portion and is locked thereto.

7. An orthodontic appliance according to claim 6, wherein the arch wire is supported in a slot in the outwardly projecting bracket, said slot being disposed between said first and second spaced portions;
   whereby as the handle is rotated to the locking position, thereby moving the locking hook into locking engagement with the bracket, the slot is covered by the locking hook thereby slidably retaining an arch wire within the slot.

8. An orthodontic appliance according to claim 6, wherein the bracket comprises spaced occlusal or gingival tie wings to which the handle is pivotally attached and to which the means for mating with the bracket is engageable and locked thereto.

9. A method of securing an arch wire to an orthodontic appliance comprising the following steps:
   modifying an occlusal or gingival tie wing edgewise arch bracket to include a rotatably attached handle member;
   positioning a locking hook in an over-center arrangement relative to the rotatably attached handle member;
   rotating the handle member to a locking position, thereby covering a slot in the occlusal or gingival tie wing edgewise arch bracket and slidably retaining an arch wire therein.

10. A method of securing an arch wire to an orthodontic appliance according to claim 9, wherein the step of modifying the occlusal or gingival tie wing edgewise arch bracket includes the steps of drilling holes in the occlusal or gingival tie wings of the bracket to rotatably mount the handle member by means of an attaching pin.

11. A method of securing an arch wire to an orthodontic appliance according to claim 9, wherein the step of positioning a locking hook in an over-center arrangement relative to the rotatably attached handle member includes the step of drilling a hole in the handle member and rotatably attaching the locking hook by means of a connecting pin.

* * * * *